United States Patent [19]

Kempf et al.

[11] Patent Number: 5,695,714
[45] Date of Patent: Dec. 9, 1997

[54] GOLD-PALLADIUM ALLOYS FOR DENTAL MATERIALS

[75] Inventors: Bernd Kempf, Freigericht; Doris Hathaway, Hanau; Gernot Schoeck, Bruchkoebel; Hans-Martin Ringelstein, Frankfurt; Bernd Meier, Hanau, all of Germany

[73] Assignee: Degussa Aktiengesellschaft, Frankfurt am Main, Germany

[21] Appl. No.: 277,623

[22] Filed: Jul. 20, 1994

[30] Foreign Application Priority Data

Jul. 23, 1993 [DE] Germany .......................... 43 24 738.5

[51] Int. Cl.⁶ .................................................. C22C 5/02
[52] U.S. Cl. .................. 420/509; 420/508; 433/200.1; 433/207
[58] Field of Search ........................ 433/207, 200.1; 420/509, 508; 148/405, 430

[56] References Cited

U.S. PATENT DOCUMENTS

| | | | |
|---|---|---|---|
| 2,050,040 | 8/1936 | Coleman et al. | 420/508 |
| 2,980,998 | 4/1961 | Coleman et al. | 420/508 |
| 3,666,540 | 5/1972 | Burnett | 117/129 |
| 3,716,356 | 2/1973 | Burnett | 420/509 |
| 4,008,080 | 2/1977 | Wagner | 420/508 |
| 4,062,676 | 12/1977 | Knosp | 420/509 |
| 4,205,982 | 6/1980 | German . | |
| 4,218,244 | 8/1980 | Knosp | 420/509 |
| 5,240,172 | 8/1993 | Steinke et al. | 420/508 |

FOREIGN PATENT DOCUMENTS

| | | | |
|---|---|---|---|
| 2828304 | 2/1979 | Germany | C22C 5/02 |
| 2755913 | 6/1979 | Germany | C22C 5/02 |
| 28 51 729 | 9/1979 | Germany . | |
| 32 11 703 | 1/1984 | Germany . | |
| 42 11 403 | 10/1993 | Germany . | |
| 488 017 | 3/1970 | Switzerland . | |

Primary Examiner—David A. Simmons
Assistant Examiner—Margery S. Phipps
Attorney, Agent, or Firm—Beveridge, DeGrandi, Weilacher & Young, LLP

[57] ABSTRACT

Gold-palladium alloys with a high gold content for dental applications should, for reasons of biocompatibility, not contain any toxically dubious components. For particularly corrosion-resistant and biocompatible Type 4 alloys, tin is needed as the only base-metal component in amounts between 0.7 and 5.8 wt % if one remains within defined limits in a palladium-tin diagram of FIG. 1, for Pt values less than 2%. Such alloys contain, in addition to gold and tin, 6 to 25 wt % palladium, 0 to 12 wt % platinum and 0 to 2 wt % of at least one of iridium, rhodium and/or ruthenium.

17 Claims, 2 Drawing Sheets

FIG. 1 Palladium–Tin Diagram

GOLD-PALLADIUM ALLOYS FOR DENTAL MATERIALS

INTRODUCTION AND BACKGROUND

The present invention relates to gold-palladium alloys with a high gold content and their use for dental castings faced with ceramic, unfaced dental castings, dental inlays, dental crowns, dental bridgework, dental prosthesis containing said dental castings, inlays, crowns, and/or bridgework, and methods of using said alloys to form said dental castings, inlays, crowns, and/or bridgework.

Permanent and removable dentures are frequently produced from corrosion-resistant, biocompatible precious-metal alloys, whereby the cast object is subsequently faced with dental ceramic so as to attain an appearance corresponding to the natural tooth. The suitability of alloys for this purpose is associated with a number of properties which have to be matched to the dental ceramic, such as coefficient of thermal expansion, melting range and adhesion between ceramic and alloy. A basic prerequisite is also good corrosion resistance and sufficient strength in order to withstand the loads arising in the chewing process. Depending on their mechanical load-carrying capacity, dental alloys are divided into various classes designated as Types 1 to 4. Type 4 alloys possess the greatest strength and therefore the broadest range of application.

The traditional alloy systems that are used for this purpose are precious-metal alloys with a high gold content. Such alloys have proved their worth clinically over many years. These alloys remain unequalled with regard to corrosion resistance and biocompatibility. But hitherto it has only been possible to meet the numerous demands, mentioned above, that are made on these alloys with alloy systems which as a rule are constructed in a very complicated manner.

The bake-on alloys with a high gold content are characterized by a gold content upwards of about 70 wt %. Palladium and platinum are as a rule added to the alloy with a view to increasing the high-temperature stability during the ceramic baking. Since platinum widens the melting range of a gold alloy significantly more than palladium, alloys which are particularly stable at high temperature can be obtained by the use, in particular, of palladium as alloy element. Such alloys as a rule have a palladium content of at least 8 wt %. A number of different base metals are added to the alloy with a view to increasing the hardness and the mechanical strength. Additional elements are added to the alloy in order to ensure the fine-tuning of additional data that are relevant from the point of view of tooth technology, such as coefficient of thermal expansion, ceramic adhesion, oxide color or sufficient ductility at high temperature. Common additional alloy elements, therefore, are silver, copper, indium, zinc, tin, iron and gallium. It is known that a number of these elements can in turn also have undesirable properties, so that attempts are made to avoid such elements or to employ them only in small amounts. For instance, silver can result in green discoloration in the case of sensitive ceramics, and copper, especially where crevice-corrosion effects occur, can result in discolorations.

Known dental alloys with a high gold content mostly contain two or more base-metal alloy elements in order to adjust all the alloy properties that are necessary for dentures.

In U.S. Pat. No. 3,716,356, a dental alloy with a high gold content is described which contains 5.5 to 40 wt % palladium and 0.03 to 1.0 wt % rhenium. In addition, up to 10 wt-% platinum, up to 2 wt % silver, up to 1 wt % iron, up to 1.5 wt % zinc, up to 2 wt % tin and up to 1 wt % indium may also be present. Hardness values for these alloys are not given, but they attain the hardness of Type 4 alloys only if additional base-metal components are present, the toxic effects of which are still largely unknown.

Dental alloys with a high gold content according to DE-OS 30 19 276 contain, besides palladium, up to 10 wt % indium and additionally ruthenium and tin in order to attain sufficient hardness values.

DE-PS 24 24 575 describes dental alloys with a high gold content containing 5 to 15 wt % platinum, 0.1 to 2 wt % indium, 0.05 to 0.5 wt % iridium and 0.5 to 3 wt % rhodium. These alloys are palladium-free.

The Type 4 dental alloys with a high gold content which are employed in practice all contain two or more base-metal components in order to attain suitable hardness values.

Within the context of a generally raised health-consciousness and a higher susceptibility to allergies and incompatibilities which is generally to be observed in people who live in modern industrial states, the biocompatibility of dental alloys has been the subject of increased discussion. Previous studies have shown that the type and amount of the components of an alloy which go into solution as a result of corrosive processes are of decisive importance for biocompatibility. The causes of the corrosion and the possible effects of the corrosion products on the organism are very complex. Studies indicate in particular that the thermal loading and oxidation of the bake-on alloys that takes place during the ceramic baking is a significant factor reducing the corrosion resistance of the alloys. In general, alloys should be aimed for in which the proportion of precious metal is as high as possible for good corrosion resistance and the number of alloy components, especially of base metals, is as low as possible in order to keep the probability of an allergic reaction to a particular component as low as possible. Of course, use should only be made of elements that are not known to have any toxic effects.

SUMMARY OF THE INVENTION

An object of the present invention is to provide gold-palladium alloys with a high gold content for dental castings faced with ceramic, unfaced dental castings, dental inlays, dental crowns, dental bridgework, which, with a view to attaining a hardness necessary for Type 4 alloys, require only a single base metal of which the toxic effect is known. In addition, these alloys should exhibit a better corrosion resistance than the alloys previously known and should possess all the other properties necessary for bake-on alloys, such as strength, ductility, coefficient of thermal expansion, ceramic adhesion and high-temperature stability.

This object and others are achieved in accordance with the present invention in that use is made of alloys which contain 6 to 25 wt % palladium, 0 to 12 wt % platinum, 0 to 2 wt % of at least one of iridium, rhodium and ruthenium, and 0.7 to 5.8 wt % tin, the remainder being gold, whereby (a) the tin content for alloys where the platinum content is below 2 wt % lies within a range which in the palladium-tin diagram (FIG. 1 discussed below) is bounded by the points A, B, C and D, where A=6 wt % Pd and 1.3 wt % Sn; B=6 wt % Pd and 2.8 wt % Sn; C=25 wt % Pd and 5.8 wt % Sn; and D=25 wt % Pd and 2.2 wt % Sn;

(b) the permitted tin content for alloys where the platinum content is above 2 wt % is decreased by 0.12 wt % tin for every 2 wt % increase in platinum content (above 2 wt %), and (c) the sum of the contents of palladium and platinum does not exceed 30 wt %.

Other objects of the invention include, but are not limited to, dental prothesis containing such dental castings faced with ceramic, unfaced dental castings, dental inlays, dental crowns, and/or dental bridgework, and also methods of using such alloys to form said dental castings, inlays, crowns, and/or bridgework.

BRIEF DESCRIPTION OF THE DRAWINGS

The present invention will be further understood with reference to the drawings, wherein.

DETAILED DESCRIPTION OF THE INVENTION

Preferred alloys of the present invention contain 12 to 25 wt % palladium, 0 to 10 wt % platinum and 0 to 2 wt % of at least one of iridium, rhodium and ruthenium by way of grain-reducing agent, 2.1 to 5.0 wt % tin, the remainder being gold, and in which the tin content lies within a range which in the palladium-tin diagram is bounded by the points A', B', C'and D, where A'=12 wt % Pd and 2.1 wt % Sn; B'=12 wt % Pd and 3.0 wt % Sn; C'=25 wt % Pd and 5.0 wt % Sn; and D has the meaning given above.

Alloys have proved particularly useful which in the palladium-tin diagram are bounded by the points A', B', C" and D", C"=16 wt % Pd and 3.5 wt % Sn; D"=16 wt % Pd and 2.2 wt % Sn; and A' and B' have the meaning given above.

Alloys have also proved particularly useful which in the palladium-tin diagram are bounded by the points A, B, C'" and D'", where C'"=10 wt % Pd and 3.4 wt % Sn; D'"=10 wt % Pd and 1.5 Sn; and A and B have the meaning given above, whereby the sum of palladium and platinum may not exceed 12 wt %.

Surprisingly, it has been shown that all the demands made on dental alloys can be met by alloys of the present invention that contain tin as the only base metal. The alloys of the present invention possess excellent corrosion resistance lying clearly above the corrosion resistance of the alloys currently known. A prerequisite for these properties is that the tin content of the alloys of the present invention is matched in a defined manner to the palladium content and, in the event of platinum being present, is also modified with respect to the platinum content. By virtue of their very good corrosion resistance and the fact that the base metal tin has been demonstrated to be harmless by its diverse use in the food industry as tinware or tin plate, the alloys of the present invention possess extraordinary biocompatibility.

Figure 1:
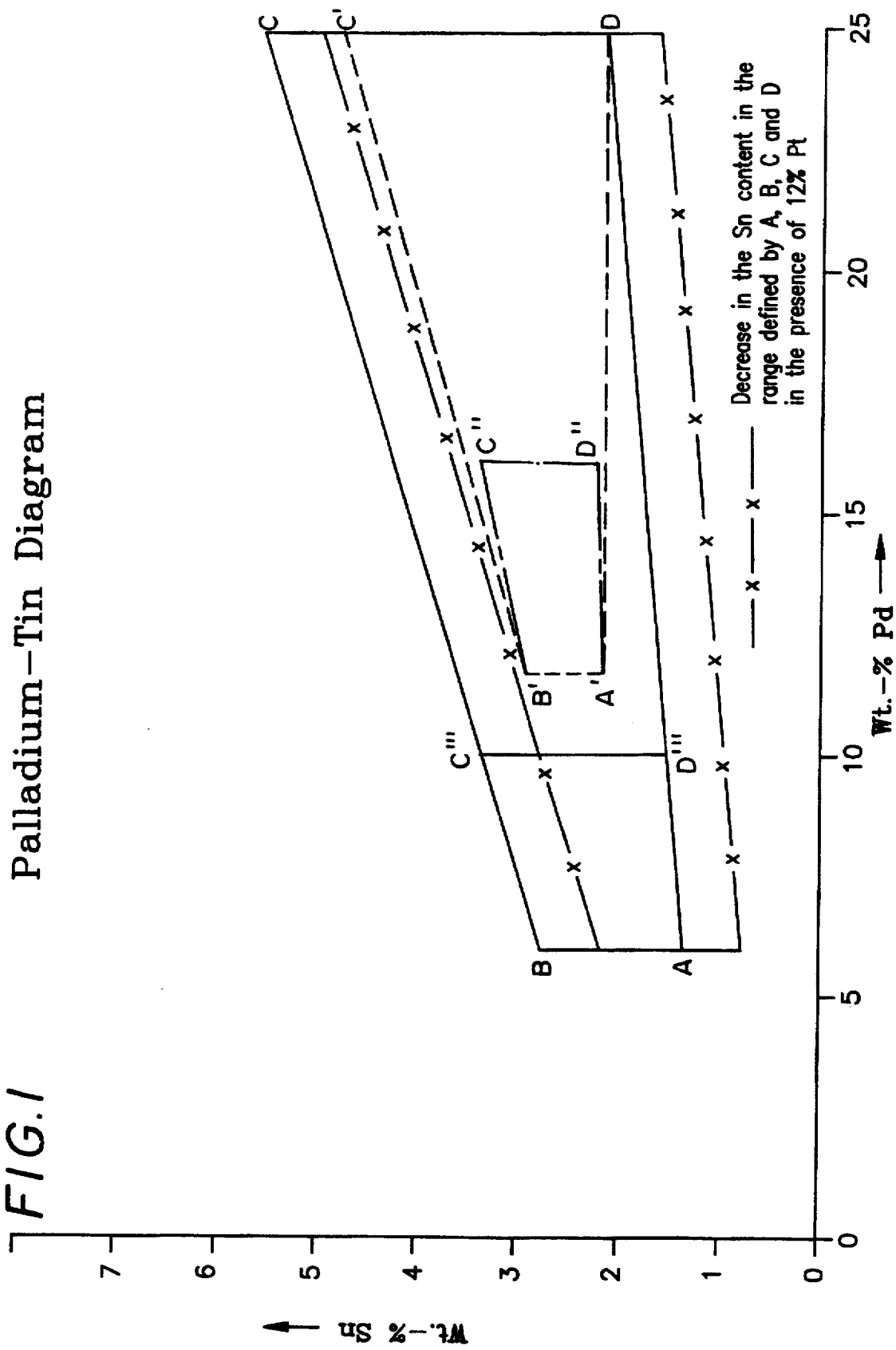
FIG. 1 is a graph of the palladium-tin contents of the alloy of the present invention.
Figure 2:
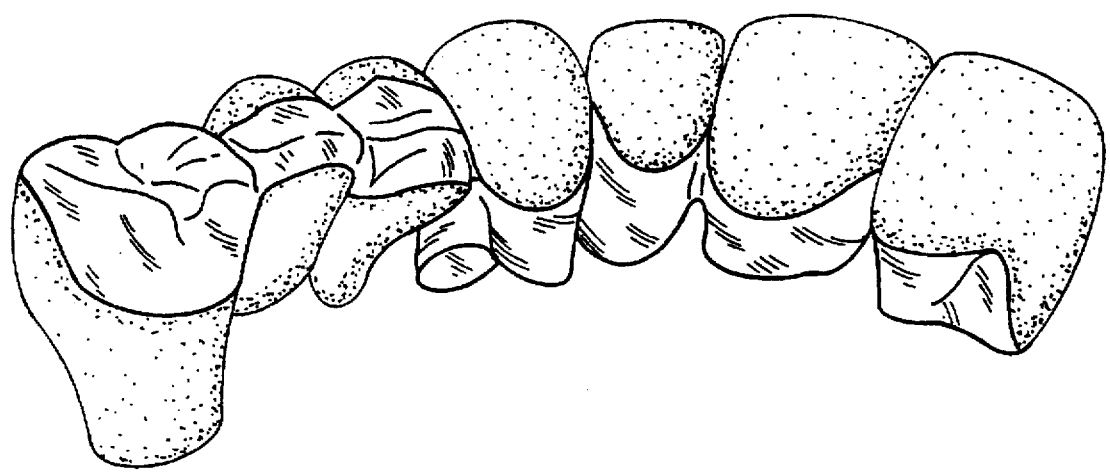
FIG. 2 is a drawing of bridgework containing the alloy of the present invention.

Alloys of the present system consist, in the simplest case, of gold, palladium and tin and can furthermore also contain 0-2% of at least one of iridium, rhodium and/or ruthenium by way of grain-reducing agent. Very good corrosion resistance and sufficient hardness for alloys of Type 4 are attained if the tin content is precisely adjusted with respect to the palladium content; specifically, the higher the palladium content of the alloy, the more tin is necessary. The possible palladium/tin ratio is represented in FIG. 1; accordingly, the permissible tin content for the permissible palladium content of 6–25% is defined by a quadrangular area in a Pd/Sn diagram, the corners of which, for a Pd content of 6 wt %, are situated at 1.3 and 2.8 wt % tin and, for a Pd content of 25 wt %, between 2.2 and 5.8 wt % tin.

The addition of platinum to the alloy has the advantage that the proportions of the base metal tin can be further reduced. The corrosion resistance and, consequently, also the biocompatibility are thereby improved still further. The addition of platinum to the alloy is limited to 12 wt %, whereby in total no more than 30 wt % palladium and platinum should be contained in the alloy; in FIG. 1, the quadrangle outlined by the ----x---- line represents the situation where the alloy contains 12 wt % Pt (the four corners of the quadrangle are as follows: 6 wt % Pd, 0.7 wt % Sn; 6 wt % Pd, 2.2 wt % Sn; 25 wt % Pd, 5.2 wt % Sn; 25 wt % Pd, 1.6 wt % Sn). For a platinum content of 2 wt % upwards the necessary tin contents can be reduced on average by 0.12 wt % for every 2 wt % platinum.

In Table 1 a number of alloys are listed in accordance with their composition. Alloys 1–6 are alloys which correspond to the state of the art. They contain at least two base metals. The amount of the other components can be calculated by adding up the sum of the listed components from which it is seen that the other components are present in only a very small amount. Alloys 7–12 represent test alloys, which in fact only contain tin by way of base metal but in which the tin content lies outside the range sketched in FIG. 1. Alloys 13–20 conform in their composition to the demands according to the present invention as regards Pd, Sn and Pt contents.

TABLE 1

Alloy compositions:

| Alloy | Au | Pd | Pt | Ag | Sn | In | Others |
|---|---|---|---|---|---|---|---|
| 1 | 77.3 | 8.9 | 9.8 | <2.0 | <2.0 | <2.0 | Cu, Fe, Re, Ir |
| 2 | 84.4 | 5.0 | 8 | — | — | 2.5 | Ta |
| 3 | 72 | 9.7 | 13 | 2.8 | 1.2 | 1.2 | Ir |
| 4 | 74.8 | 15 | 6 | — | 2 | 2 | Ir |
| 5 | 86 | — | 10.4 | — | — | <2.0 | Rh, Ta |
| 6 | 77.7 | — | 19.5 | — | — | — | Zn, Ta |
| 7 | 64.9 | 25 | 4 | — | 6.0 | — | 0.1 Ru |
| 8 | 77.8 | 20 | — | — | 1.8 | — | 0.4 Ru |
| 9 | 83.3 | 15 | — | — | 1.5 | — | 0.2 Ir |
| 10 | 91 | 7.5 | — | — | 1.3 | — | 0.2 Ir |
| 11 | 88.8 | 7.5 | — | — | 3.5 | — | 0.2 Ir |
| 12 | 75.4 | 14 | 6 | — | 4.5 | — | 0.1 Ir |
| 13 | 72.8 | 23 | — | — | 4.0 | — | 0.2 Ir |
| 14 | 81.5 | 15 | — | — | 3.0 | — | 0.5 Ir |
| 15 | 77.8 | 14 | 6 | — | 2.1 | — | 0.1 Ir |
| 16 | 81.8 | 14 | 2 | — | 2.0 | — | 0.2 Ir |
| 17 | 76.8 | 13 | 8 | — | 2.2 | — | |
| 18 | 86.8 | 10 | — | — | 2.0 | — | 1.2 Rh |
| 19 | 89.1 | 7 | 2 | — | 1.8 | — | 0.1 Ir |
| 20 | 81.3 | 14.5 | — | — | 4.0 | — | 0.2 Ir |

The results of corrosion trials are compiled in Table 2. In order to determine the corrosion resistance, corrosion tests were carried out in accordance with Draft DIN (German Industrial Standard) 13927. To this end, test bodies of the alloys to be tested are stored for 7 days in a solution of 0.1M lactic acid and 0.1M common salt at 37° C. Then the corrosive solution is analyzed qualitatively and quantitatively by means of suitable analytical procedures known in the art with regard to the corrosion products released. In order to exclude surface effects and the influence of oxidation, subsequent to a previously simulated ceramic baking the test bodies are abraded before they are placed in the corrosive solution. In the trials carried out, besides this "standard corrosion test", more stringent test conditions were additionally chosen so that the influence of oxidation on the corrosion reaction could be precisely examined. This is necessary since it has to be assumed that under real conditions it is not possible for the whole set of dentures to be reworked mechanically after the ceramic baking in such a way that the preceding oxidative damage to the unfaced regions is completely removed. In order to simulate these conditions, selected alloys were sandblasted and oxidized and, without subsequent removal of the oxide layer, suspended in the corrosive solution.

In Table 2 the concentrations of the dissolved alloy components are listed which were analyzed in each case. The final column lists, in addition, the sum of the total ion concentrations, which constitutes the essential criterion in Draft DIN 13927. Specifically, the sum of all dissolved ions after 7 days of corrosion may not exceed the limiting value of 100 µg/cm². The rates of corrosion of the elements which lie below the particular detection limit (0.13 µg/cm²) are not taken into account in the total value.

TABLE 2

Concentrations of dissolved elements in the corrosion solutions in µg/cm².

| Alloy No. | Au | Pd | Pt | Ag | Sn | In | Others | Total concentrations |
|---|---|---|---|---|---|---|---|---|
| Standard corrosion test ||||||||| 
| 1 | <0.13 | <0.13 | <0.13 | <0.13 | <0.13 | 0.50 | | 0.50 |
| 2 | <0.04 | <0.13 | <0.13 | — | | 0.39 | | 0.39 |
| 4 | <0.13 | <0.13 | <0.13 | — | 0.14 | 0.62 | | 0.76 |
| 6 | <0.13 | | <0.13 | — | | | Zn: 20.8 | 20.8 |
| 13 | <0.13 | <0.13 | — | — | 0.17 | — | | 0.17 |
| 14 | <0.13 | <0.13 | <0.13 | — | <0.13 | — | | 0 |
| 15 | <0.13 | <0.13 | <0.13 | — | <0.13 | — | | 0 |
| 18 | <0.13 | <0.13 | <0.13 | — | <0.13 | — | | 0 |
| 19 | <0.13 | <0.13 | <0.13 | — | <0.13 | — | | 0 |
| 20 | <0.13 | <0.13 | <0.13 | — | <0.13 | — | | 0 |
| More stringent test conditions: ||||||||| 
| 1 | <0.13 | <0.13 | 0.35 | 0.13 | 0.77 | 5.8 | Cu: 3.4; Fe: 0.47 | 10.8 |
| 2 | <0.13 | <0.13 | <0.13 | — | — | 8.79 | — | 8.79 |
| 4 | <0.13 | <0.13 | <0.13 | — | 1.4 | 6.2 | | 7.6 |
| 13 | <0.13 | <0.13 | <0.13 | — | 0.38 | | | 0.38 |
| 14 | <0.13 | <0.13 | <0.13 | — | 0.52 | — | — | 0.52 |
| 15 | <0.13 | <0.13 | <0.13 | — | <0.13 | — | | 0 |
| 19 | <0.13 | <0.13 | <0.13 | — | <0.13 | — | | 0 |
| 20 | <0.13 | <0.13 | <0.13 | — | <0.13 | — | — | 0 |

The results prove that the bake-on alloys with a high gold content all possess corrosion values which lie far below the prescribed limiting values. It is surprising, however, that only with the alloys according to the present invention do all analyzed elements lie below or just above the particular detection limit. Under the more stringent corrosion conditions, this difference between the alloys representing the state of the art and the alloys according to the present invention becomes even more apparent. Whereas the alloys according to the state of the art exhibit a significant increase in the corrosion data, the alloys according to the present invention exhibit, even under these stringent conditions, only very low rates of corrosion. The analyzed elements even lie mostly below the particular detection limit.

The outstanding stability of the alloys according to the present invention with respect to oxidation, to which the good corrosion resistance can probably be attributed, is also substantiated by metallographic and thermogravimetric investigations using methods known in the art. On metallographic microsections in the case of the alloys according to the state of the art, it is possible to detect pronounced internal oxidation zones, whereas in the case of the alloys according to the present invention the strips of oxide are so thin that they are almost undetectable under an optical microscope. The oxidation of the alloys results in a weight gain which can be determined thermogravimetrically. To this end, from a number of alloys thin rings were cast so as to present as large a surface as possible to the corroding oxygen. Suspended on a thermobalance, these rings were heated, at a definite heating rate of 30 K/min, up to 950° C., maintained at this temperature for 120 min and then cooled, again at a constant cooling rate of 30 K/min. During the test the weight gain was measured continuously. Table 3 lists the total weight gains which represent a measure of the oxidation that has taken place. The alloys according to the present invention (Nos. 14, 15, 17, 19) are characterized by the lowest weight gains.

TABLE 3

Weight gains through oxidation

| Alloy No. | Weight Gain (mg/cm²) |
|---|---|
| 1 | 0.58 |
| 2 | 0.69 |
| 3 | 0.38 |
| 5 | 0.66 |
| 4 | 0.46 |
| 14 | 0.29 |
| 15 | 0.26 |
| 17 | 0.24 |
| 19 | 0.21 |

With a view to characterizing the strength at room temperature, Table 4 lists the hardness values subsequent to casting, in the hardened state and after kiln treatment, as well as the yield point, the tensile strength and the elongation at break. The tensile test samples were heat-treated in accordance with Draft DIN 13927, so that a structure was available such as that existing after the ceramic baking.

TABLE 4

Hardness values and mechanical strength

| Alloy No. | HV cast | HV hard | HV kiln | Rp[MPa] | Rm[MPa] | A(%) |
|---|---|---|---|---|---|---|
| 1 | 193 | 225 | 200 | 490 | 630 | 10.5 |
| 2 | 170 | 220 | 180 | 480 | 590 | 8.2 |
| 4 | 203 | 250 | 205 | 569 | 701 | 5.2 |
| 6 | 202 | 230 | 190 | | | |
| 7 | 210 | 235 | 225 | 573 | 638 | 1.8 |
| 8 | 86 | | 90 | | | |
| 9 | 115 | 128 | | | | |
| 10 | 125 | 127 | | | | |
| 11 | 185 | | 193 | 488 | 530 | 1.4 |
| 12 | 175 | | 187 | 518 | 543 | 1.9 |
| 13 | 206 | 228 | 216 | | | |
| 14 | 200 | 216 | 231 | 572 | 693 | 5.4 |
| 15 | 182 | 223 | 202 | 558 | 696 | 7.6 |
| 16 | 193 | | 196 | 534 | 673 | 6.1 |
| 17 | 178 | | 169 | | | |
| 18 | 194 | | 172 | 488 | 562 | 5.7 |
| 19 | 153 | | 164 | | | |
| 20 | 206 | | 190 | | | |

The test alloys (8, 9, 10) with tin contents lying below the range according to the present invention exhibit only low hardness and strength values. Although the test alloys (Nos. 7, 11, 12) which exhibit tin contents that are too high possess high hardness values and tensile strengths, their ductility is too low. As metallographic trials show, the formation of a second phase is responsible for this.

The measurements with regard to the high-temperature stability of the alloys are compiled in Table 5. The high-temperature stability of the alloys during the ceramic baking is defined by the so-called sag resistance (i.e., the resistance to deformation at high temperature on the basis of the dead weight). In order to determine the sag resistance, test rods with dimensions 50 mm×3 mm×1 mm were produced by investment casting and were cleansed of potting medium by sandblasting. To simulate the ceramic baking, the test samples were subjected to a 20-minute heat treatment at 980° C., whereby they were stored on two ceramic supports lying horizontally on the flat side. The ceramic supports were spaced by 40 mm so that the possibility existed that the test samples would bend under their own weight. The extent of the bending was ascertained by measuring the test rods before and after the ceramic baking by means of an inductive displacement-sensing system known in the art. The difference in the bending before and after the ceramic baking represents a measure of the high-temperature stability. As can be seen from Table 5, the alloys without any palladium content or with small palladium contents exhibit strong bending (alloy Nos. 5 and 6). Alloys with relatively high palladium contents are significantly more stable at high temperature. Particularly good high-temperature stabilities are exhibited by the alloys (Nos. 13, 15 and 17) with palladium contents higher than 12%.

TABLE 5

Results of sag resistance test

| Alloy No. | Bending in μm (average values) |
|---|---|
| 1 | 98 |
| 2 | 420 |
| 4 | 60 |
| 5 | 790 |
| 6 | 880 |
| 13 | 75 |
| 15 | 43 |
| 17 | 38 |
| 18 | 330 |
| 19 | 460 |

Alloys with palladium contents below 12 wt % do not have quite such good strength properties at high temperatures (alloy Nos. 18 and 19), but these alloys have the advantage that they still exhibit a yellow or yellowish color which is preferred for aesthetic reasons.

Terms such as dental castings faced with ceramic, unfaced dental castings, dental inlays, dental crowns, and dental bridgework are well known in this art.

Further variations and modifications of the foregoing will be apparent to those skilled in the art and such variations and modifications are attended to be encompassed by the claims that are appended hereto.

What is claimed:

1. A gold-palladium alloy with a high gold content for dental castings faced with ceramic and for unfaced dental castings, said alloy consisting of 6 to 25 wt % palladium, 0 to 12 wt % platinum, 0 to 2 wt % of at least one member of the group consisting of iridium, rhodium and ruthenium, and 0.7 to 5.8 wt-% tin, the remainder being gold, wherein
   (a) said tin content of said alloy where said alloy contains less than 2 wt % platinum lies within a range defined in the palladium-tin diagram according to FIG. 1 wherein the quadrangle is bounded by the points A, B, C and D, wherein point A is at 6 wt % Pd and 1.3 wt % Sn, point B is at 6 wt % Pd and 2.8 wt % Sn, point C is at 25 wt % Pd and 5.8 wt % Sn, and point D is at 25 wt % Pd and 2.2 wt % Sn;
   (b) said tin content of said alloy where said alloy contains more than 2 wt % platinum is decreased from the Sn range defined in the palladium-tin diagram according to FIG. 1 by 0.12 wt % tin for every 2 wt % increase in platinum content, and
   (c) the sum of the contents of palladium and platinum does not exceed 30 wt %.

2. The gold-palladium alloy according to claim 1, comprising 12 to 25 wt % palladium, 0 to 10 wt % platinum, and 0 to 2 wt % of at least one member of the group consisting of iridium, rhodium and ruthenium, 2.1 to 5.0 wt % tin, the remainder being gold, wherein said tin content of said alloy where said alloy contains less than 2 wt % platinum lies within a range defined in the palladium-tin diagram according to FIG. 1 wherein the quadrangle is bounded by the points A', B', C' and D, wherein point A' is at 12 wt % Pd and 2.1 wt % Sn, point B' is at 12 wt % Pd and 3.0 wt % Sn, point C' is at 25 wt % Pd and 5.0 wt % Sn, and point D is at 25 wt % Pd and 2.2 wt % Sn.

3. The gold-palladium alloy according to claim 1, wherein the tin content of said alloy where said alloy contains less than 2 wt % platinum lies within a range defined in the palladium-tin diagram according to FIG. 1 wherein the quadrangle is bounded by the points A', B', C" and D", wherein point A' is at 12 wt % Pd and 2.1 wt % Sn, point B' is at 12 wt % Pd and 3.0 wt % Sn, point C" is at 16 wt % Pd and 3.5 wt % Sn, and point D" is at 16 wt % Pd and 2.2 wt % Sn.

4. The gold-palladium alloy according to claim 1, comprising 6 to 10 wt % palladium, 0 to 6 wt % platinum, 0 to 2 wt % of at least one member of the group consisting of iridium, rhodium and ruthenium, 1.3 to 3.4 wt % tin, the remainder being gold, wherein the tin content of said alloy where said alloy contains less than 2 wt % platinum lies within a range defined in the palladium-tin diagram according to FIG. 1 wherein the quadrangle is bounded by the points A, B, C'" and D'", wherein point A is at 6 wt % Pd and 1.3 wt % Sn, point B is at 6 wt % Pd and 2.8 wt % Sn, point C'" is at 10 wt % Pd and 3.4 wt % Sn, and point D'" is at 10 wt % Pd and 1.5 wt % Sn, and the sum of palladium and platinum does not exceed 12 wt %.

5. The gold-palladium alloy according to claim 1, wherein said tin content of said alloy where said alloy contains 12 wt % platinum lies within a range defined in the palladium-tin diagram according to FIG. 1 wherein the quadrangle is outlined by ----x---- and is bounded by the points 6 wt % Pd, 0.7 wt % Sn; 6 wt % Pd, 2.2 wt % Sn; 25 wt % Pd, 5.2 wt % Sn; and 25 wt % Pd, 1.6 wt % Sn.

6. A dental casting comprising the gold-palladium alloy according to claim 1 optionally faced with ceramic.

7. A dental prosthesis comprising the dental casting according to claim 6.

8. A method of using the gold-palladium alloy according to claim 1, comprising forming a dental casting with said gold-palladium alloy optionally faced with ceramic.

9. A dental inlay comprising the gold-palladium alloy according to claim 1.

10. A dental prosthesis comprising the dental inlay according to claim 9.

11. A method of using the gold-palladium alloy according to claim 1, comprising forming a dental inlay with said gold-palladium alloy.

12. A dental crown comprising the gold-palladium alloy according to claim 1.

13. A dental prosthesis comprising the dental crown according to claim 12.

14. A method of using the gold-palladium alloy according to claim 1, comprising forming a dental crown with said gold-palladium alloy.

15. A dental bridgework comprising the gold-palladium alloy according to claim 1.

16. A dental prosthesis comprising the dental bridgework according to claim 15.

17. A method of using the gold-palladium alloy according to claim 1, comprising forming a dental bridgework with said gold-palladium alloy.

* * * * *